(12) United States Patent
Pierry

(10) Patent No.: US 9,702,794 B2
(45) Date of Patent: Jul. 11, 2017

(54) USER REPLACEABLE FILTER FOR GAS SAMPLING SYSTEM

(71) Applicant: KONINKLIJKE PHILIPS N.V., Eindhoven (NL)

(72) Inventor: Anthony Pierry, Plantsville, CT (US)

(73) Assignee: Koninklijke Philips N.V., Eindhoven (NL)

( * ) Notice: Subject to any disclaimer, the term of this patent is extended or adjusted under 35 U.S.C. 154(b) by 88 days.

(21) Appl. No.: 14/368,369

(22) PCT Filed: Dec. 13, 2012

(86) PCT No.: PCT/IB2012/057279
§ 371 (c)(1),
(2) Date: Jun. 24, 2014

(87) PCT Pub. No.: WO2013/098693
PCT Pub. Date: Jul. 4, 2013

(65) Prior Publication Data
US 2014/0326081 A1    Nov. 6, 2014

Related U.S. Application Data

(60) Provisional application No. 61/580,339, filed on Dec. 27, 2011.

(51) Int. Cl.
*G01N 1/22* (2006.01)
*G01N 1/24* (2006.01)
*B01D 46/00* (2006.01)

(52) U.S. Cl.
CPC ............... *G01N 1/24* (2013.01); *B01D 46/00* (2013.01); *G01N 1/2205* (2013.01); *G01N 1/2247* (2013.01); *G01N 2001/2244* (2013.01)

(58) Field of Classification Search
None
See application file for complete search history.

(56) References Cited

U.S. PATENT DOCUMENTS

| 5,328,664 | A |   | 7/1994 | Ponsy |
| 5,553,507 | A |   | 9/1996 | Basch et al. |
| 5,717,147 | A | * | 2/1998 | Basch ................. G01N 1/2205 73/863.23 |
| 5,993,743 | A |   | 11/1999 | Nordman et al. |
| 6,022,510 | A | * | 2/2000 | Springmann ........ G01N 1/2258 422/534 |
| 6,126,724 | A |   | 10/2000 | Martin et al. |
| 6,138,521 | A |   | 10/2000 | Basch et al. |
| 7,010,991 | B2 |   | 3/2006 | Lutz et al. |

(Continued)

FOREIGN PATENT DOCUMENTS

| CN | 2692652 A | 4/2005 |
| JP | S4616206 B1 | 5/1971 |

(Continued)

*Primary Examiner* — Robert R Raevis

(57) ABSTRACT

A replaceable filter integrated into the front panel accessory interconnect system of a gas sampling system includes a filter body mounted within a housing of the system. The filter body is insertable into a filter receptacle, and removable from the filter receptacle by a twist-lock mechanism. The filter body includes an integral accessory receptacle. An accessory connector is insertably connectable with the accessory receptacle.

15 Claims, 4 Drawing Sheets

(56) References Cited

U.S. PATENT DOCUMENTS

| | | |
|---|---|---|
| 7,597,733 B2 | 10/2009 | Fudge et al. |
| 2010/0159575 A1 | 6/2010 | Chen |
| 2011/0283884 A1 | 11/2011 | Larsen et al. |
| 2014/0326081 A1 | 11/2014 | Pierry |

FOREIGN PATENT DOCUMENTS

| | | |
|---|---|---|
| JP | S5135096 A | 3/1976 |
| JP | H108338793 A | 12/1996 |
| JP | 2003185609 A | 7/2003 |

\* cited by examiner

USER REPLACEABLE FILTER FOR GAS SAMPLING SYSTEM

CROSS-REFERENCE TO PRIOR APPLICATIONS

This application is the U.S. National Phase application under 35 U.S.C. §371 of International Application No. PCT/IB2012/057279, filed on Dec. 13, 2012, which claims the benefit of U.S. Provisional Patent Application No. 61/580,339, filed on Dec. 27, 2011. These applications are hereby incorporated by reference herein.

TECHNICAL FIELD

The inventive concepts described herein generally relate to a replaceable filter for a gas sampling system. More particularly, the inventive concepts relate to a replaceable filter that is insertable into a filter receptacle and that includes an integral accessory receptacle for removable connection with an accessory connector.

BACKGROUND

Gas detection and measurement systems typically collect a sample of gas or a continuous stream of gas from a desired sample site through a tube, and the sample is in turn provided to a measurement apparatus for analysis. In many applications such as respiratory gas monitoring, water and other contaminants may be present in the gases collected and monitored. Various types of filters and water traps are often employed at one or more points along the sample tube to prevent such contaminants from being drawn inside the measurement apparatus, to thus prevent the contaminants from interfering with measurement of the sample and/or occluding the path of gas to the measurement apparatus. Such filters and water traps are often located externally of the measurement apparatus on an instrument panel near where the sample tube is connected to the apparatus, so that the user may readily access the filters for replacement when excessively contaminated. In other cases, such filters may be located internally of the measurement apparatus, thus requiring the instrument to be serviced if the filter needs to be replaced.

Filters and water traps placed near an instrument panel are often an acceptable solution to allowing easy filter replacement. However, an external filter and water trap requires extra space beyond what is needed for the sample line connector. Often the additional space required is not available. For example, many multi-parameter medical monitoring instruments have several plug-in modules in close proximity to one another, or a compact cluster of sensor connectors. In such cases, the additional space needed to locate an external filter poses a significant problem. On the other hand, locating the filter internally of the measurement apparatus creates the problem that the instrument user cannot change the filter when needed, with the result that the measurement apparatus must be taken out of service for maintenance to replace the filter.

Thus, there is a need in the art for a gas sampling system including a replaceable filter that can be removed by a user and that has a sample line accessory connector integrated with the replaceable filter, so that no additional external space other than that needed for the sample line accessory connector is needed.

SUMMARY

In accordance with an example embodiment, a gas sampling apparatus is provided including a filter receptacle; and a filter body configured to be insertable into the filter receptacle, the filter body having: an accessory receptacle integral with the filter body and connectable to a removable accessory connector to receive a gas supply, and a filter that filters the gas supply to provide a filtered gas sample to the filter receptacle.

In accordance with another example embodiment, a gas sampling apparatus is provided that includes a housing including a front panel; a filter receptacle mounted within the housing and accessible through the front panel; a filter body configured to be insertable into the filter receptacle, the filter body having: an accessory receptacle integral with the filter body and connectable to a removable accessory connector to receive a gas supply, and a filter that filters the gas supply to provide a filtered gas sample to the filter receptacle; a pump connected to the filter receptacle to draw the filtered gas sample into a sample line for analysis; and a sensor configured to detect a state of the filter body to provide a signal that actuates the pump.

It should be appreciated that all combinations of the foregoing concepts and additional concepts discussed in greater detail below (provided such concepts are not mutually inconsistent) are contemplated as being part of the inventive concepts disclosed herein. In particular, all combinations of claimed subject matter appearing at the end of this disclosure are contemplated as being part of the inventive concepts disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the inventive concepts.

DETAILED DESCRIPTION

In the following detailed description, for purposes of explanation and not limitation, representative embodiments disclosing specific details are set forth in order to provide a thorough understanding of the present teachings. However, it will be apparent to one having ordinary skill in the art having had the benefit of the present disclosure that other embodiments according to the present teachings that depart from the specific details disclosed herein remain within the scope of the appended claims. Moreover, descriptions of well-known apparatuses and methods may be omitted so as to not obscure the description of the representative embodiments. Such methods and apparatuses are clearly within the scope of the present teachings.

Figure 1:
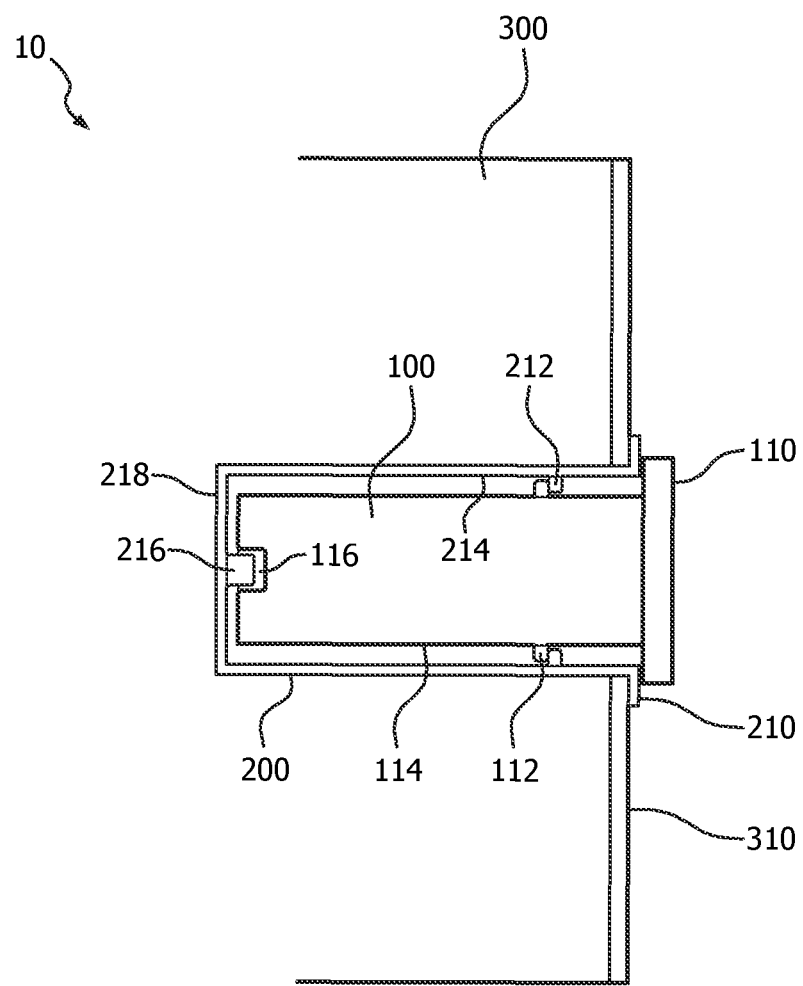
FIG. 1 is a cross-sectional view illustrating a gas sampling apparatus including a filter body with an integral accessory receptacle, the filter body inserted into a filter receptacle mounted within the gas sampling apparatus, according to a representative embodiment.

FIG. 1 is a cross-sectional view illustrating a gas sampling apparatus including a filter body with an integral accessory receptacle, the filter body inserted into a filter receptacle mounted within the gas sampling apparatus, according to a representative embodiment.

In FIG. 1, gas sampling apparatus 10 is shown in part as including filter receptacle 200 mounted within housing 300, with filter body 100 inserted into filter receptacle 200 through an opening in instrument panel 310. Filter receptacle 200 extends into housing 300, and is formed as an enclosure including a sidewall 214. It should be understood that FIG. 1 is a cross-sectional view with sidewall 214 partially cut-away to show filter body 100 as inserted into the interior of filter receptacle 200. That is, in this representative embodiment, sidewall 214 may be substantially continuous to form an enclosure that may be of cylindrical shape. Filter body 100 may also be of general cylindrical shape so as to conformally fit within filter receptacle 200. The front or open end of filter receptacle 200 may include a substantially continuous flange 210 extending from a first end of sidewall 214. Flange 210 may be fixedly secured to the exterior of instrument panel 310 along the opening in instrument panel 310. Rear wall 218 may be fixedly secured to the second end of sidewall 214, to enclose filter receptacle 200. Tubing connector 216 may be disposed as protruding through rear wall 218 to engage filter body 100 upon insertion of filter body 100 into filter receptacle 200 as will be subsequently described. Filter receptacle 200 as noted above thus forms an enclosure within housing 300 that is accessible through the opening in instrument panel 310, and that substantially isolates any additional components within housing 300 from the interior of filter receptacle 200, preventing any of contact of the additional components with liquids, solids, and/or a user.

Figure 2:
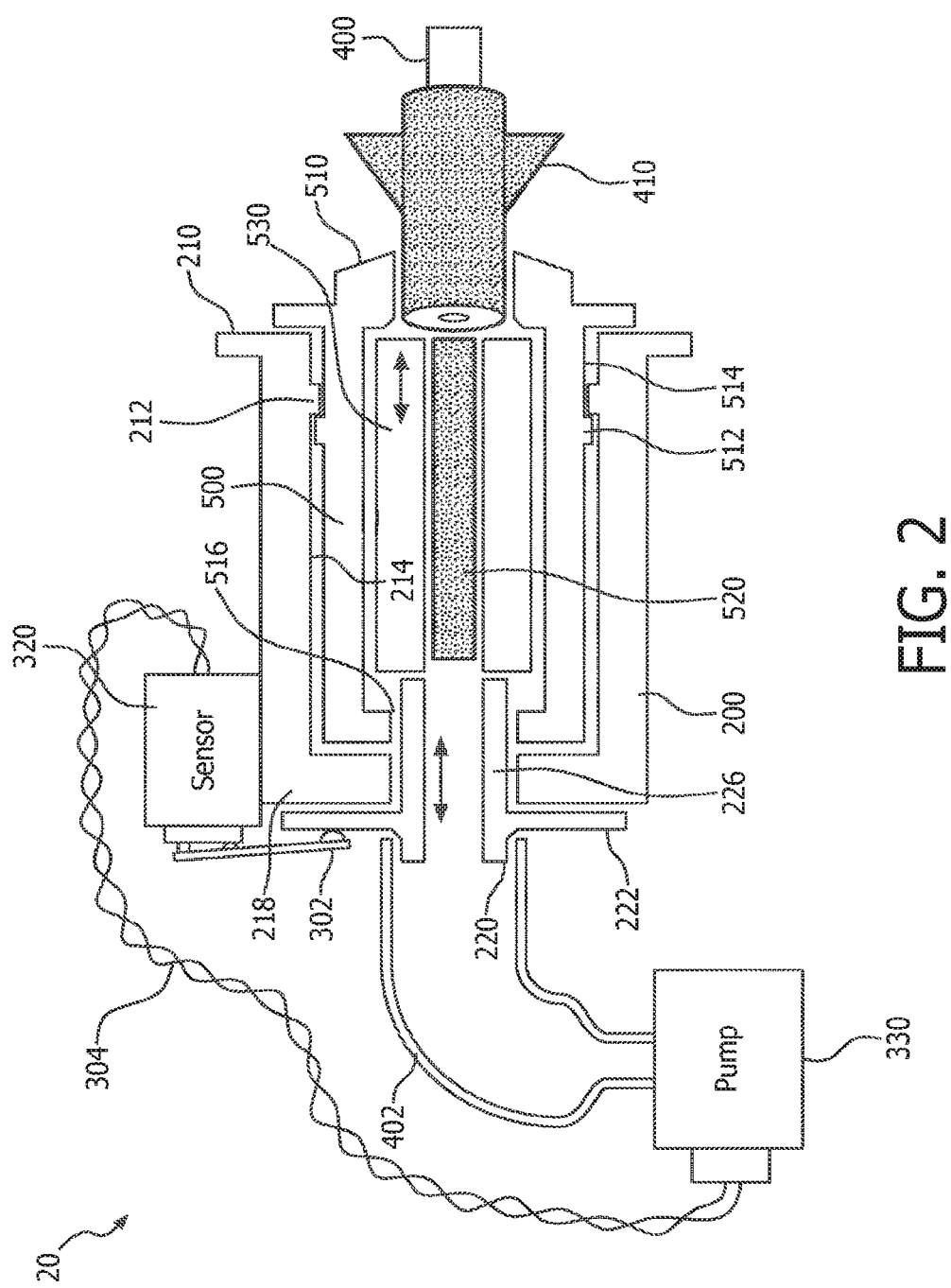
FIG. 2 is a cross-sectional view illustrating a gas sampling apparatus including a filter body with an integral accessory receptacle, the filter body inserted into a filter receptacle mounted within the gas sampling apparatus, and a sensor for detecting insertion of an accessory connector into the accessory receptacle, according to another representative embodiment.

Filter body 100 is removably insertable into filter receptacle 200, and includes accessory receptacle 110 integral with a first end of filter body 100. Accessory receptacle 110 is configured to be connectable with an accessory connector (not shown in FIG. 1) to receive gas for sampling. Incidentally, for example, an accessory connector such as accessory connector 410 disposed at the end of sample line 400 as shown in FIG. 2 may be removably connected to accessory receptacle 110 for providing a gas supply, as will be described subsequently. Accessory receptacle 110 may be configured to be connectable with any of variety of standard accessory connectors. As noted, accessory receptacle 110 is formed as integral with filter body 100, as either molded directly to or as part of filter body 100 (as shown in FIG. 2), and/or as fixedly attached directly to filter body 100. The diameter of accessory receptacle 110 as shown in FIG. 1 is greater than the diameter of the opening in instrument panel 310. The second end of filter body 100 may include outlet port 116 that provides a filtered gas sample from filter body 100. Upon insertion of filter body 100 completely within filter receptacle 200 as shown in FIG. 2, outlet port 116 and tubing connector 216 are engaged, accessory receptacle 110 is abutted against flange 210 and/or the exterior surface of instrument panel 310, and substantially the only part of filter body 100 accessible at instrument panel 310 is accessory receptacle 110.

As further shown in FIG. 1, first lock tabs 112 are disposed as protruding sections from sidewall 114 of filter body 100, and second lock tabs 212 are disposed as protruding sections from sidewall 214 within filter receptacle 200. First and second lock tabs 112 and 212 cooperate to form a twist-lock type mechanism holding filter body 100 in place within filter receptacle 200. Upon insertion of filter body 100 into filter receptacle 200, filter body 100 may be rotated in either direction (clockwise or counter-clockwise) so that the first and second lock tabs 112 and 212 are not aligned with each other and may thus move laterally past each other unimpeded, and so that filter body 100 may be inserted entirely within filter receptacle 200. Thereafter, filter body 100 may be further rotated in either direction so that the side surfaces of first and second lock tabs 112 and 212 abut one another in a lateral direction, locking filter body 100 within filter receptacle 200. Filter body 100 may be removed from filter receptacle 200 by rotating filter body 100 in either direction so that first and second lock tabs 112 and 212 are no longer aligned with each other and so that filter body 100 may be withdrawn laterally from filter receptacle 200.

FIG. 2 is a cross-sectional view illustrating a gas sampling apparatus including a filter body with an integral accessory receptacle, the filter body inserted into a filter receptacle mounted within the gas sampling apparatus, and a sensor for detecting insertion of an accessory connector into the accessory receptacle, according to another representative embodiment.

Referring to FIG. 2, gas sampling apparatus 20 is shown as including similar features as in FIG. 1 respectively denoted by similar reference numerals. In this representative embodiment however, gas sampling apparatus 20 is shown in part as including filter body 500 removably insertable into filter receptacle 200. FIG. 2 is a cross-sectional view with sidewall 214 of filter receptacle 200 partially cut-away to show filter body 500 as fully inserted into the interior of filter receptacle 200. That is, in this representative embodiment, sidewall 214 may be substantially continuous to form an enclosure that may be of cylindrical shape. In FIG. 2, various components are disposed in a similar manner as shown in FIG. 1, and detailed description of such similar components may be omitted from the following for the sake of brevity. Also, housing 300 and instrument panel 310 as shown in FIG. 1 are omitted from FIG. 2 to simplify FIG. 2. As should be understood, flange 210 may be fixedly secured to the exterior of the instrument panel (not shown) along an opening in the instrument panel.

In FIG. 2, filter body 500 is also shown in cross-section, and includes accessory receptacle 510 integral with filter body 500 and disposed at a first end of sidewall 514. Accessory connector 410 as disposed at the end of sample line 400 is removably connectable to accessory receptacle 510, and is shown in FIG. 2 as fully inserted into accessory receptacle 510. The interior of filter body 500 in this representative embodiment includes slidable inner filter tube 530 which houses filter 520. Slidable inner filter tube 530 is displaceable in a lateral direction within filter body 500 responsive to insertion and connection of accessory connector 410 with accessory receptacle 510. The second end of filter body 500 may include outlet port 516. As further shown, first lock tabs 512 are disposed as protruding sections from sidewall 514 of filter body 500, and second lock tabs 212 are disposed as protruding sections from sidewall 214 within filter receptacle 200, as similarly described with respect to FIG. 1.

Tubing connector 226 in FIG. 2 is disposed through rear wall 218 of filter receptacle 200, and extends into outlet port 516 of filter body 500 when filter body 500 is fully inserted into filter receptacle 200. Tubing connector 226 of this representative embodiment is a slidable actuator tube that is displaceable in the lateral direction as shown, responsive to displacement of slidable inner filter tube 530 within filter body 500. At the exterior of rear wall 218 of filter receptacle 200, tubing connector 226 further includes a barbed connector 220 providing a connection point to sample line 402 which leads to pump 330 within the housing (not shown) of gas sampling apparatus 20. Pump 330 draws the filtered gas sample from tubing connector 226 along sample line 402, and the drawn filtered gas sample is subsequently provided to a measurement device (not shown) for analysis. Tubing connector 226 further includes flange 222 which extends from barbed connector 220 along rear wall 218 of filter receptacle 200. Sensor 320 may be mounted within the housing on or near an exterior of filter receptacle 200 in proximity of rear wall 218, and includes actuator arm 302 which is in contact with flange 222 of tubing connector 226.

Upon insertion and connection of accessory connector 410 with accessory receptacle 510 of fully inserted filter body 500 as shown in FIG. 2, slidable inner filter tube 530 is laterally displaced against tubing connector 226 which extends through outlet port 516 into filter body 500. Tubing connector 226 is slidably displaced in a lateral direction responsive to displacement of slidable inner filter tube 530, and actuator arm 302 of sensor 320 is consequently translated into a displaced position by flange 222 of tubing connector 226. Sensor 320 provides a pump actuator signal to pump 330 via conductive lines 304 to actuate pump 330. Accordingly, sensor 320 actuates pump 330 responsive to insertion and connection of accessory connector 410 of sample line 400 to accessory receptacle 510 of filter body 500, and thus prolongs service life of pump 330 and protects the measurement device, by preventing operation of pump 330 when gas sampling apparatus 20 is not connected to a gas source.

Figure 3:
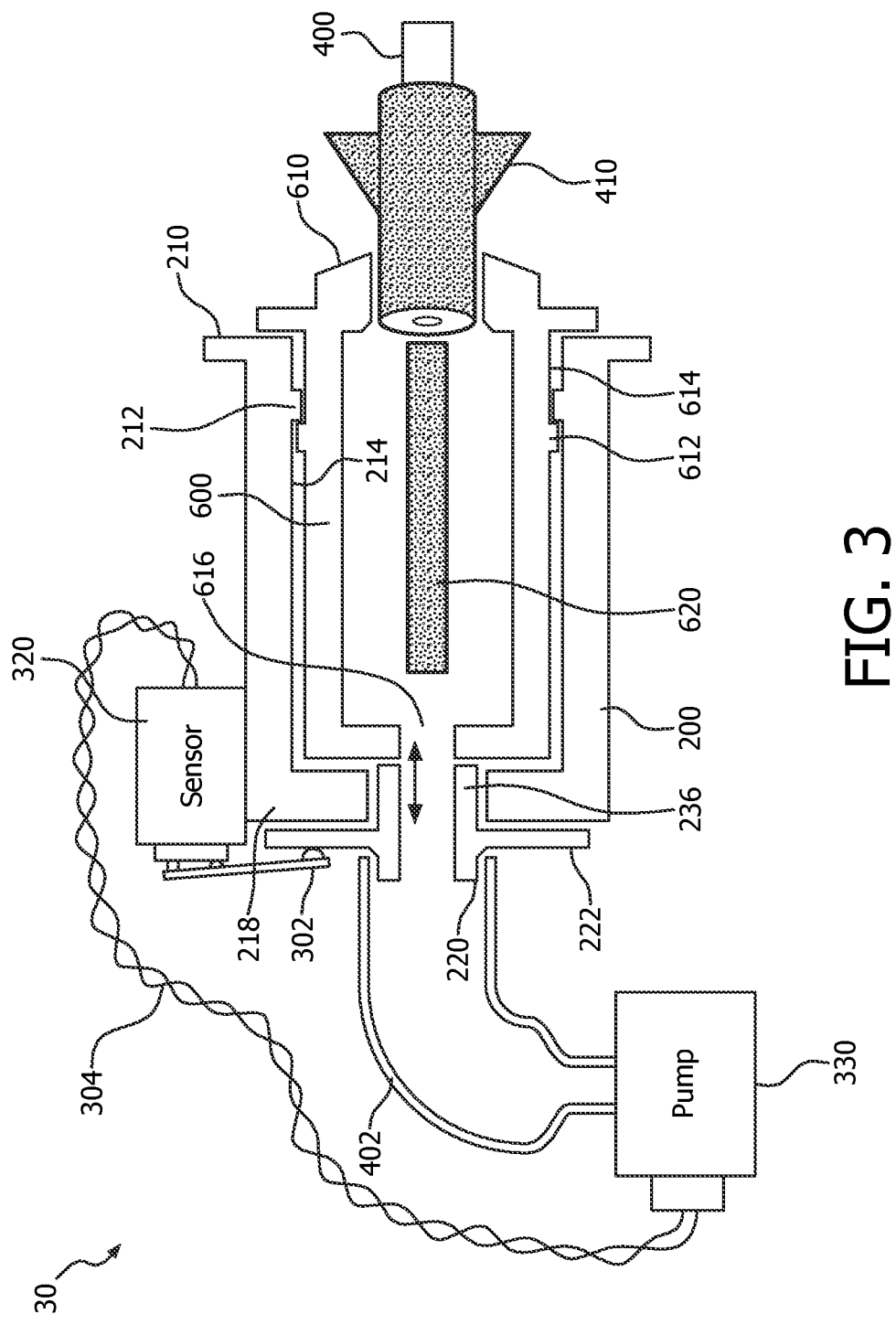
FIG. 3 is a cross-sectional view illustrating a gas sampling apparatus including a filter body with an integral accessory receptacle, the filter body inserted into a filter receptacle mounted within the gas sampling apparatus, and a sensor for detecting insertion of the filter body into the filter receptacle, according to another representative embodiment.

FIG. 3 is a cross-sectional view illustrating a gas sampling apparatus including a filter body with an integral accessory receptacle, the filter body inserted into a filter receptacle mounted within the gas sampling apparatus, and a sensor for detecting insertion of the filter body into the filter receptacle, according to another representative embodiment.

Referring to FIG. 3, gas sampling apparatus 30 is shown as including similar features as in FIG. 2 respectively denoted by similar reference numerals. In this representative embodiment however, gas sampling apparatus 30 is shown in part as including filter body 600 removably insertable into filter receptacle 200. FIG. 3 is a cross-sectional view with sidewall 214 of filter receptacle 200 partially cut-away to show filter body 600 as fully inserted into the interior of filter receptacle 200. That is, in this representative embodiment, sidewall 214 may be substantially continuous to form an enclosure that may be of cylindrical shape. In FIG. 3, various components are disposed in a similar manner as shown in FIG. 2, and detailed description of such similar components may be omitted from the following for the sake of brevity. Also, housing 300 and instrument panel 310 as shown in FIG. 1 are omitted from FIG. 3 to simplify FIG. 3. As should be understood, flange 210 may be fixedly secured to the exterior of the instrument panel (not shown) along an opening in the instrument panel.

In FIG. 3, filter body 600 is also shown in cross-section, and includes accessory receptacle 610 integral with filter body 600 and disposed at a first end of sidewall 614. Accessory connector 410 as disposed at the end of sample line 400 is removably connectable to accessory receptacle 610, and is shown in FIG. 3 as fully inserted into accessory receptacle 610. The interior of filter body 600 in this representative embodiment houses filter 620. In contrast to the representative embodiment of FIG. 2, filter 620 is stationary and not displaceable within filter body 600. The second end of filter body 600 may include outlet port 616. As further shown, first lock tabs 612 are disposed as protruding sections from sidewall 614 of filter body 600, and second lock tabs 212 are disposed as protruding sections from sidewall 214 within filter receptacle 200, as similarly described with respect to FIG. 1.

Tubing connector 236 in FIG. 3 is disposed through rear wall 218 of filter receptacle 200. However, in contrast to the representative embodiment of FIG. 2, tubing connector 236 does not extend into outlet port 616 of filter body 600 when filter body 600 is fully inserted into filter receptacle 200. That is, the diameter of outlet port 616 of filter body 600 in FIG. 3 is reduced in comparison to the diameter of outlet port 516 of filter body 500 in FIG. 2, so that tubing connector 236 in FIG. 3 is abutted against the second end of filter body 600 when filter body 600 is fully inserted into filter receptacle 200. Tubing connector 236 of this representative embodiment is a slidable actuator tube that is displaceable in the lateral direction as shown, responsive to full insertion of filter body 600 within filter receptacle 200. At the exterior of rear wall 218 of filter receptacle 200, tubing connector 236 further includes a barbed connector 220 providing a connection point to sample line 402 which leads to pump 330 within the housing (not shown) of gas sampling apparatus 30. Pump 330 draws the filtered gas sample from tubing connector 236 along sample line 402, and the drawn filtered gas sample is subsequently provided to a measurement device (not shown) for analysis. Tubing connector 236 further includes flange 222 which extends from barbed connector 220 along rear wall 218 of filter receptacle 200. Sensor 320 may be mounted within the housing on or near an exterior of filter receptacle 200 in proximity of rear wall 218, and includes actuator arm 302 which is in contact with flange 222 of tubing connector 236.

Upon full insertion of filter body 600 into filter receptacle 200 as shown in FIG. 3, filter body 600 is abutted against tubing connector 236. Tubing connector 236 is slidably displaced in a lateral direction responsive to abutment with filter body 600, and actuator arm 302 of sensor 320 is consequently translated into a displaced position by flange 222 of tubing connector 236. Sensor 320 provides a pump actuator signal to pump 330 via conductive lines 304 to actuate pump 330. Accordingly, sensor 320 actuates pump 330 responsive to full insertion of filter body 600 into filter receptacle 200, and thus prolongs service life of pump 330 and protects the measurement device, by preventing operation of pump 330 when filter body 600 is not fully and/or properly inserted into filter receptacle 200.

While several representative embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein.

For example, the representative embodiment of FIG. 1 is described whereby gas sampling apparatus 10 includes filter receptacle 200 formed as an enclosure within housing 300, with filter body 100 insertable into filter receptacle 200 through an opening in instrument panel 310. In a further representative embodiment, the combination of filter receptacle body 200 and filter body 100 may be disposed exteriorly of housing 300.

Figure 4:
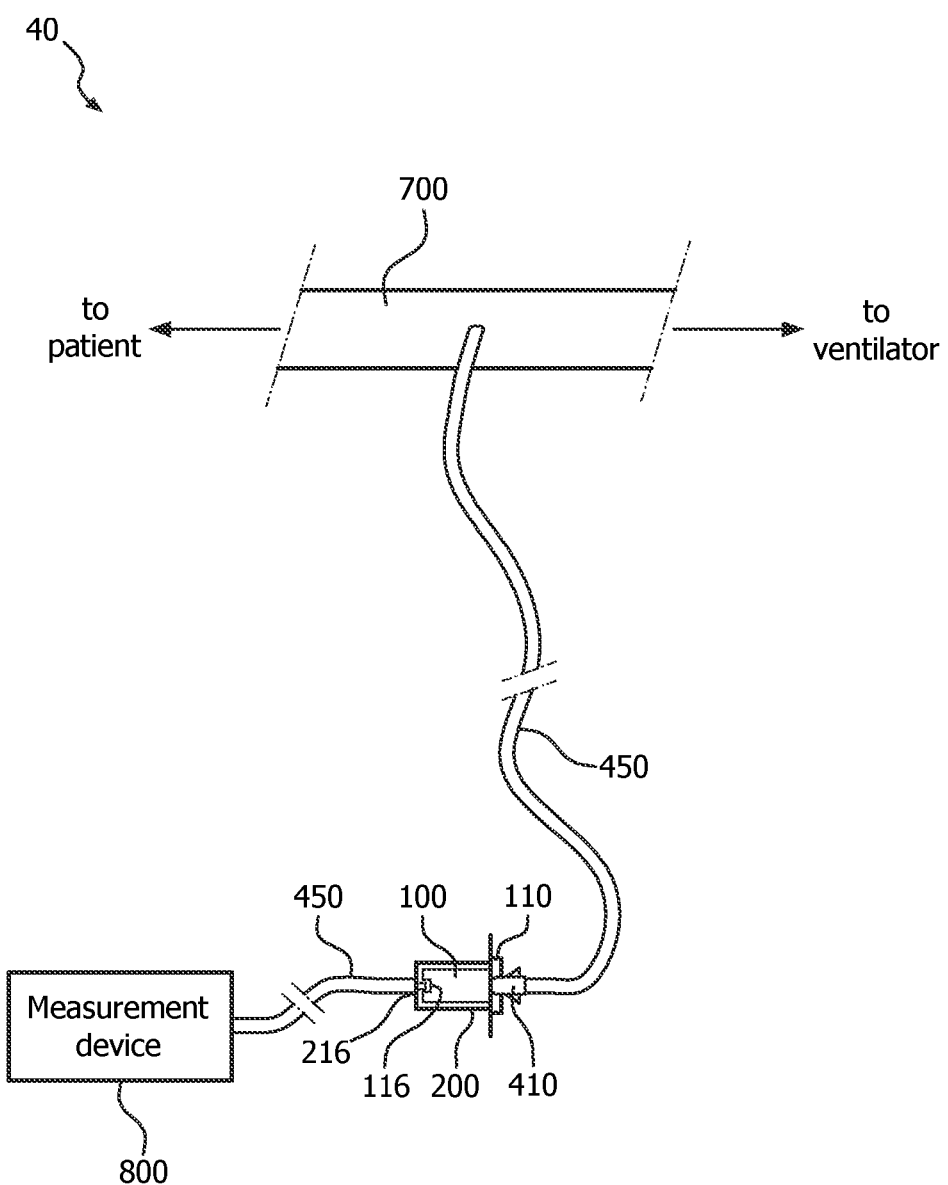
FIG. 4 is a simplified diagram illustrating the combination of a filter receptacle and filter body disposed directly in a sample line between a breathing circuit and a measurement device, according to another representative embodiment.

FIG. 4 is a simplified diagram illustrating the combination of a filter receptacle and filter body disposed directly in a sample line between a breathing circuit and a measurement device, according to another representative embodiment.

As shown in FIG. 4, gas sampling apparatus 40 includes the combination of filter receptacle 200 and filter body 100 disposed directly in sample line 450 between breathing circuit 700 and measurement device 800. Initially, it should be understood that FIG. 4 is not drawn to scale, and that the components may be exaggerated to further understanding. In FIG. 4, filter body 100 is removably insertable into filter receptacle 200. Accessory receptacle 110 is integral with a first end of filter body 100. Accessory connector 410 at an end of sample line 450 that leads to breathing circuit 700, may be removably inserted into accessory receptacle 110. The filtered gas sample may be provided from filter body 100 to tubing connector 216 through outlet port 116 of filter body 100. An end of sample line 450 that leads to measurement device 800 may be connected to tubing connector 216 by connector barbs (not shown), and the filtered gas sample may be delivered from tubing connector 216 to measurement device 800 via the corresponding section of sample line 450. In this further representative embodiment, the combination of filter receptacle 200/filter body 100 may be conveniently disposed anywhere along sample line 450, reducing complexity and space necessary at measurement device 800.

In the representative embodiments of FIGS. 1-3, filter receptacle 200 is described as mounted within the housing of a gas sampling apparatus. In further representative embodiments, filter receptacle 200 may instead be mounted within the housing of a rack including multi-parameter medical monitoring instruments having several plug-in modules in close proximity to one another, or within the housing of a multi-parameter medical instrument containing a gas sampling apparatus and including a cluster of sensor connectors.

In the representative embodiments of FIGS. 1-3, the filter receptacle 200 and the various filter bodies are described generally as having cylindrical shape. However, in further representative embodiments, filter receptacle 200 and the various filter bodies may have various other shapes and designs, whereby the filter bodies are provided to be securely insertable within filter receptacle 200. Also, various other locking mechanisms such as a threaded screw-type interlock, or a hook and latch mechanism requiring depressing of a release lever to uncouple the filter body from filter receptacle 200, may be used to maintain the filter bodies within filter receptacle 200. In still further representative embodiments, sensors 320 in FIGS. 2 and 3 may determine the respective state of the filter bodies within filter receptacle 200 optically, or magnetically using a magnet on the filter receptacle or the filter body and a hall-effect sensor.

Those skilled in the art should also readily appreciate that all parameters, dimensions, materials, and configurations described herein are meant to be exemplary and that the actual parameters, dimensions, materials, and/or configurations will depend upon the specific application or applications for which the representative embodiments is/are used. Those skilled in the art will recognize, or be able to ascertain using no more than routine experimentation, many equivalents to the specific representative embodiments described herein. It is, therefore, to be understood that the foregoing embodiments are presented by way of example only and that, within the scope of the appended claims and equivalents thereto, representative embodiments may be practiced otherwise than as specifically described and claimed. Representative embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A gas sampling apparatus comprising:
a filter receptacle; and
a filter body removably inserted in filter receptacle, the filter body comprising (i) an accessory receptacle integral with the filter body at a first end of the filter body and connectable to a removable accessory connector to receive a gas supply, the accessory receptacle being the only portion of the filter body that protrudes from the filter receptacle when the filter body is fully inserted into the filter receptacle, and (ii) a filter configured to filter the received gas supply and to output a filtered gas sample from a second end of the filter body, opposite the first end, through the filter receptacle.

2. The apparatus of claim 1, wherein the filter receptacle is mounted in a measurement system and is directly accessible through an instrument panel of the measurement system.

3. The apparatus of claim 2, wherein the filter receptacle has an open end through which the filter body is insertable, the open end of the filter receptacle including a flange mounted on the instrument panel.

4. The apparatus of claim 1, wherein the filter body further comprises an outlet port integral with the filter body and configured to output the filtered gas sample from the filter body, and the filter receptacle comprises a tubing connector that is connectable with the outlet port to receive the filtered gas sample when the filter body is fully inserted into the filter receptacle.

5. The apparatus of claim further comprising a locking mechanism including first protrusions on an inner wall of the filter receptacle and second protrusions on a sidewall of the filter body, the first protrusions configured to be respectively engageable with the second protrusions to lock the filter body into the filter receptacle upon rotation of the filter body inserted into the filter receptacle.

6. The apparatus of claim 1, further comprising a sensor in contact with a portion of the filter receptacle, the sensor detecting when the filter body is fully inserted in the filter receptacle, and providing a pump actuator signal to a pump when the filter body is detected as being fully inserted in the filter receptacle.

7. The apparatus of claim 6, wherein the filter receptacle comprises a tubing connector that is connectable with the filter body to receive the filtered gas sample when the filter body is fully inserted into the filter receptacle, the tubing connector being displaceable upon insertion of the filter body into the filter receptacle, and
wherein the sensor is configured to provide the pump actuation signal responsive to displacement of the tubing connector.

8. The apparatus of claim 1, further comprising a sensor configured to detect insertion of the accessory connector into the accessory receptacle to provide a pump actuator signal.

9. The apparatus of claim 8, wherein the filter receptacle comprises a tubing connector that is connectable with the filter body to receive the filtered gas sample when the filter body is fully inserted into the filter receptacle, the filter configured to slide within the filter body upon insertion of the accessory connector into the accessory receptacle to displace the tubing connector, and
wherein the sensor is configured to provide the pump actuation signal responsive to displacement of the tubing connector.

10. The apparatus of claim 1, disposed in a sample line between a breathing circuit and a measurement device.

11. The apparatus of claim 1, further comprising:
a housing including a front panel, wherein the filter receptacle is mounted within the housing and accessible through the front panel;
a pump connected to the filter receptacle to draw the filtered gas sample into a sample line for analysis; and
a sensor structured and configured to detect a state of the filter body to provide a signal that actuates the pump.

12. The apparatus of claim 11, wherein the filter body further comprises an outlet port integral with the filter body that outputs the filtered gas sample from the second end of the filter body, and the filter receptacle comprises a tubing connector that is connectable with the outlet port to receive the filtered gas sample when the filter body is fully inserted into the filter receptacle.

13. The apparatus of claim 11, further comprising a locking mechanism including first protrusions on an inner wall of the filter receptacle and second protrusions on a sidewall of the filter body, the first protrusions configured to be respectively engageable with the second protrusions to lock the filter body into the filter receptacle upon rotation of the filter body inserted into the filter receptacle.

14. The apparatus of claim 11, wherein the filter receptacle comprises a tubing connector that is connectable with the filter body to receive the filtered gas sample when the filter body is fully inserted into the filter receptacle, the filter configured to slide within the filter body upon insertion of the accessory connector into the accessory receptacle to displace the tubing connector, and
wherein the sensor is configured to provide the signal that actuates the pump responsive to displacement of the tubing connector.

15. The apparatus of claim 11, wherein the filter receptacle comprises a tubing connector that is connectable with the filter body to receive the filtered gas sample when the filter body is fully inserted into the filter receptacle, the tubing connector configured to be displaceable upon insertion of the filter body into the filter receptacle, and
wherein the sensor is configured to provide the signal that actuates the pump responsive to displacement of the tubing connector.

* * * * *